United States Patent [19]

Weyrauch et al.

[11] Patent Number: 5,270,210
[45] Date of Patent: Dec. 14, 1993

[54] CAPACITIVE SENSING SYSTEM AND WASH/ALIGNMENT STATION FOR A CHEMICAL ANALYZER

[75] Inventors: Bruce Weyrauch, Newman Lake; Leon Schmidt; Dan Cutler, both of Spokane, all of Wash.

[73] Assignee: Schiapparelli Biosystems, Inc., Fairfield, N.J.

[21] Appl. No.: 916,223

[22] Filed: Jul. 16, 1992

[51] Int. Cl.$^5$ .................. G01N 35/00; G01N 21/00; G01N 31/00; G01N 33/00
[52] U.S. Cl. ........................ 436/43; 436/180; 436/808; 422/64; 422/67; 422/82.03; 422/82.05; 422/82.08; 422/82.09; 422/100; 422/105; 422/108; 73/863.32; 356/246
[58] Field of Search .............. 422/64, 63, 67, 82.03, 82.05, 82.08, 82.09, 100, 105, 108; 436/43, 180, 808; 356/246; 73/863.32

[56] References Cited

U.S. PATENT DOCUMENTS

| 3,391,547 | 7/1968 | Kingston | 62/218 |
|---|---|---|---|
| 3,635,094 | 1/1972 | Oberli | 73/243 |
| 3,754,444 | 8/1973 | Ure et al. | 73/423 |
| 4,276,258 | 6/1981 | Ginsberg et al. | 422/64 |
| 4,276,260 | 6/1981 | Drbal et al. | 422/100 |
| 4,326,851 | 4/1982 | Bello et al. | 23/230 R |
| 4,389,900 | 6/1983 | Gutierrez | 73/861.42 |
| 4,487,836 | 12/1984 | Takayanagi et al. | 436/2 |
| 4,736,638 | 4/1988 | Okawa et al. | 73/864.24 |
| 4,818,492 | 4/1989 | Shimizu | 422/110 |
| 4,897,244 | 1/1990 | Wallace et al. | 422/100 |
| 4,961,906 | 10/1990 | Andersen et al. | 422/102 |
| 4,970,468 | 11/1990 | Ishizawa et al. | 324/662 |
| 5,051,238 | 9/1991 | Umetsu et al. | 422/64 |
| 5,130,254 | 7/1992 | Collier et al. | 436/54 |

Primary Examiner—James C. Housel
Assistant Examiner—N. Bhat
Attorney, Agent, or Firm—Wells, St. John, Roberts, Gregory & Matkin

[57] ABSTRACT

The automatic chemical analyzer includes a turntable adapted to hold a plurality of disposable cuvettes. An optical system adjacent to the turntable can perform tests on the contents of each cuvette as they are rotated on the turntable. A sample/reagent tray is rotatably mounted about an axis parallel to the turntable axis. A common probe arm pivoted about a third parallel axis mounts a pipette that can be moved along an arcuate path intersecting a cuvette access station on the turntable and at least one container access station on the sample/reagent tray for transferring liquids as required by specific test procedures. A wash/alignment station is provided to facilitate flushing on the pipette between liquid deliveries. Combined within it is an alignment plate that checks the radial position of the pipette relative to the probe arm axis and the elevation of the pipette tip relative to the supporting instrument framework. A capacitive sensing system is used to detect liquid level elevations during liquid transfers. It also is used for pipette alignment purposes.

20 Claims, 9 Drawing Sheets

CAPACITIVE SENSING SYSTEM AND WASH/ALIGNMENT STATION FOR A CHEMICAL ANALYZER

TABLE OF CONTENTS

System Overview
Wash/Alignment Station
Capacitive Sensing System

TECHNICAL FIELD

This disclosure pertains to a clinical chemistry analyzer for testing of patient samples, such as blood or urine. It generally relates to automatic chemical analyzers for directly measuring properties of reacted liquids to produce qualitative and quantitative analyses of tested samples. It specifically pertains to a capacitive sensing system for measuring liquid levels within such instruments and to a wash/alignment station for cleaning of a movable pipette and periodically checking its physical orientation relative to the instrument.

BACKGROUND OF THE INVENTION

Automated analyzers have been developed for biochemical analysis of patient samples, such as whole blood, serum, urine, plasma and cerebral spinal fluid. Most such equipment available today is complicated to operate, large in size and high in cost.

The operation of such equipment is technically complicated. It typically requires specialized operators to be available at all times, with commensurate personnel expenses being encountered. It is usually designed for use by large laboratories serving a wide geographic area or by a large medical facility. These existing analyzers carry out tests in a defined sequence of operations designed for efficient, high volume usage.

Such large scale capacity is not always required, particularly in smaller medical clinics where large volumes of blood samples are not encountered on a daily basis. The present chemical analyzer was developed to meet the practical needs of smaller medical settings. It is designed as a desk-top unit that can be operated without specialized laboratory training. Its throughput is adequate for meeting typical clinical applications. As an example, it can be designed to produce a maximum of 164 test results per hour for routine, single reagent chemistries. To provide a representative wide number of reagents, the analyzer has been designed to have a capacity of 40 reagent containers of two different sizes on board. Its capacity can be effectively doubled by utilizing two of the chemistry instruments in tandem, both being controlled by a common workstation.

The compact nature of the analyzer can be partially attributed to the fact that a single probe arm and pipette service all of the functional liquid-handling components included within it. The common pipette is used for transferring samples and reagents, as well as for diluting liquids as needed by particular test requirements.

To obtain large volumes of tests, conventional laboratory analyzers are programmed to conduct test procedures in a fixed sequence of events. While predetermined test sequences are practical in high volume chemical analyzer applications, there is a need for more flexible operation when scaling such test procedures to meet the needs of smaller medical facilities.

The present invention provides testing flexibility by permitting random access to each cuvette on a test turntable and to each container (cups, wells and reagent bottles) on a sample/reagent tray. It is therefore not necessary for the instrument to sequence through any predetermined processing steps-the controlling software can tailor the required steps to the tests currently requisitioned. This permits a greater number of tests to be conducted while using a minimum number of containers, cuvettes and reagent bottles. The software controls the sequencing of tests based upon predetermined priority schedules, rather than defined test sequences dictated by the nature of the tests being conducted.

The automated controls for the present chemical analyzer minimize operator training and required skill levels. Sample and reagent sensing that occurs automatically during operation of the analyzer notifies the operator of depleted liquid conditions as they occur.

A unique capacitive sensing system is used for sensing liquid levels. Capacitive sensing of liquid levels is used within the chemistry instrument to maintain updated inventory information.

The use of one movable pipette to handle a variety of liquids (samples, regents and/or diluents) requires the ability to rapidly clean the pipette between each fluid delivery involving a new fluid. In addition, the pipette must be constantly checked to assure that it is properly aligned in a vertical orientation and is accurately located elevationally.

According to this disclosure, the capacitive sensing system used to monitor liquid levels in the instrument is also used in conjunction with a probe alignment module to monitor both radial and axial positioning of the pipette relative to the movable probe support. These procedures detect bent conditions prior to damage of associated equipment. Elevational alignment is critical because the pipette is used to measure liquid levels during operation of the instrument.

Further details concerning the system will be evident from the following description.

BRIEF DESCRIPTION OF THE DRAWINGS

The preferred embodiment of the invention is illustrated in the accompanying drawings, in which:

FIG. 13 is a block wiring diagram of the sensing circuit;

FIG. 14 is a simplified equivalent circuit diagram; and

DETAILED DESCRIPTION OF THE PREFERRED EMBODIMENT

This disclosure of the invention is submitted in furtherance of the constitutional purposes of the U.S. Patent Laws "to promote the progress of science and useful arts" (Article 1, Section 8).

System Overview

The automatic chemical analyzer (generally illustrated in FIGS. 1–3) includes a turntable 11 rotatably mounted about a first vertical axis. A plurality of disposable cuvettes 10 are releasably mounted to the turntable 11. A first power means, shown as motor 12, is operably connected to turntable 11 for alternately (1) indexing it at a stationary angular position about the first axis with a selected cuvette 10 positioned at a cuvette access station A or (2) turning it about the first axis while mixing or centrifuging contents of cuvettes mounted to it.

Figure 1:
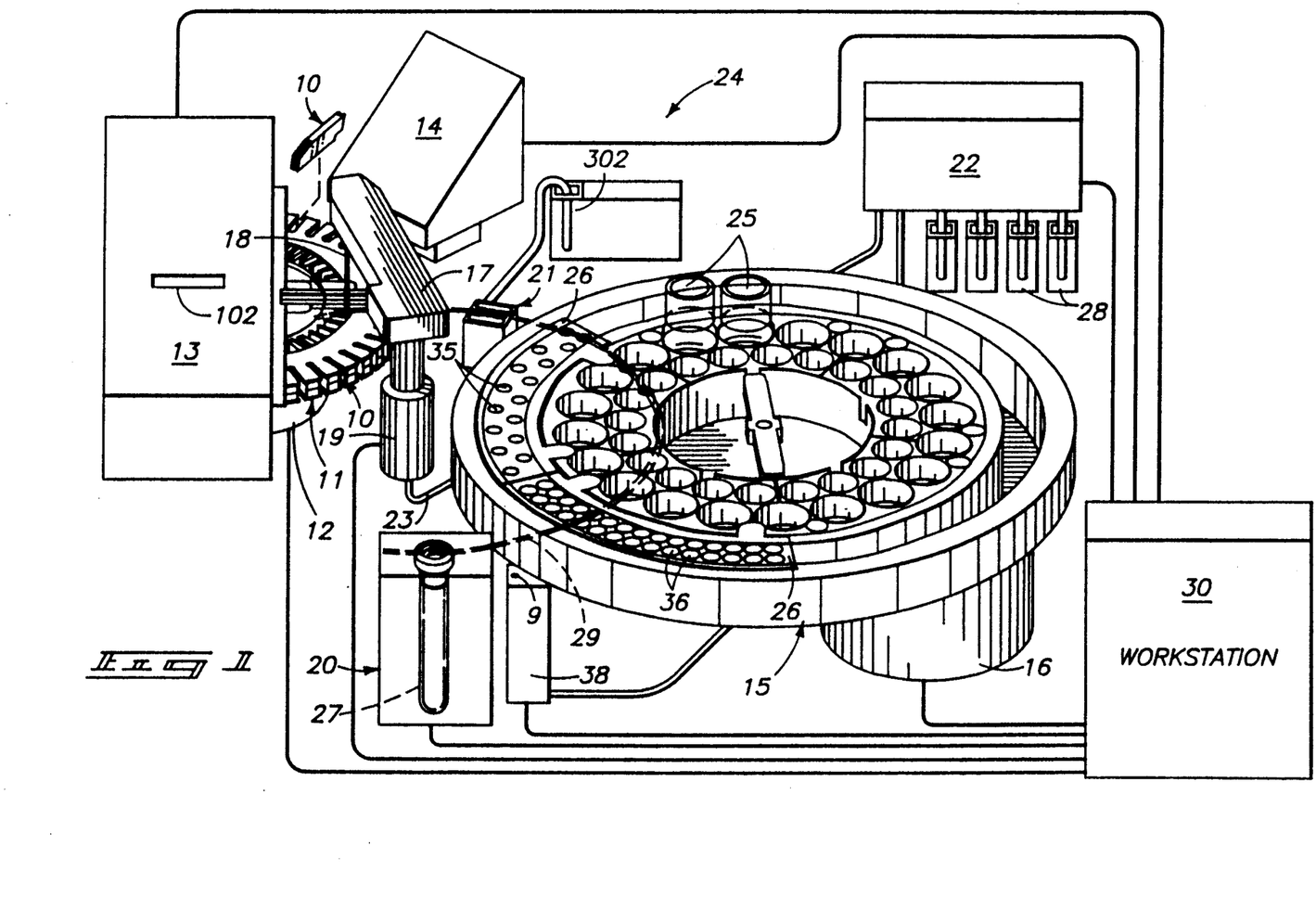
FIG. 1 is a diagrammatic perspective view of the principal components in the analyzer.
Figure 2:
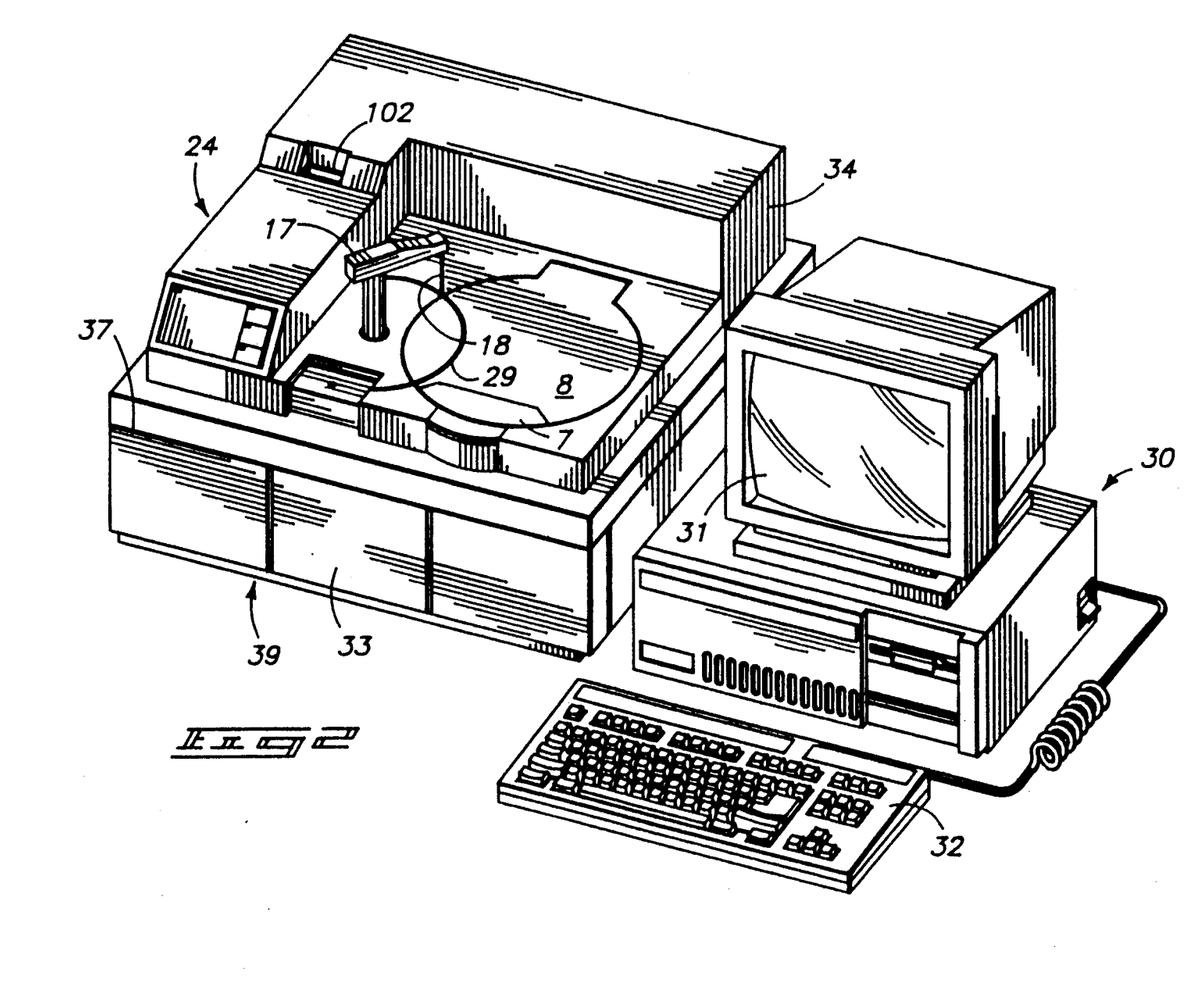
FIG. 2 is a perspective view of the analyzer.

First analytical means, illustrated as an optical system 14, is provided adjacent to the turntable 11 for performing tests on the contents of the cuvettes 10 as they rotate about the turntable axis.

A tray 15 is rotatably mounted about a second vertical axis parallel to and spaced from the first axis. A plurality of containers 25, 35, and 36 are positioned about tray 15 for reception of samples and reagent liquids. Second power means, illustrated as motor 16, is operably connected to the tray 15. The motor 16 indexes tray 15 to a stationary angular position about the second axis with a selected container positioned at a container access station C.

The analyzer also includes a probe arm 17 movable about a third vertical axis parallel to the first axis. Probe arm 17 supports a downwardly-extending open pipette 18. The vertical pipette 18 is movable along an arcuate path centered about the third axis and intersecting both the cuvette access station A and container access station C. It can move along the arcuate path in a random fashion to transfer liquid from a container positioned on the tray at the container access station C to a cuvette 10 positioned on the turntable 11 at the cuvette access station A. The arcuate path of the pipette 18 can be visualized along a protective groove 29 formed at the exterior of the enclosure 39 housing the chemistry instrument 24.

The illustrated embodiment of the clinical chemistry analyzer consists of two major components: a chemistry instrument 24 and a workstation 30. The chemical instrument accepts liquid patient samples for testing purposes, performs appropriate optical and/or potentiometric measurements on the samples, and communicates the resulting test data to workstation 30. Workstation 30 is used by the operator to enter data, control operation of instrument components, accept data generated by the instrument, manage and maintain system information, and generate visual and printed reports about assays and instrument performance.

The chemistry instrument 24 is a separate unit with minimal operator controls. Either one or two identical chemistry instruments 24 can be linked to a single workstation 30, as required in a particular setting. The chemistry instrument 24 can perform several types of analysis. These include routine chemistries, electrolytes, therapeutic drug monitoring, drugs of abuse in urine, and other specialized tests.

The liquid-handling components that make up the chemistry instrument 24 are housed within enclosure 39 (FIGS. 2–5). It separates along a peripheral parting line 37 defining a lower supporting base 33 and an upper hinged cover 34.

The principal modular components of the chemistry instrument 24 are diagrammatically illustrated in FIG. 1. The illustrated components are specifically designed for use in association with a specially designed liquid cuvette 10.

A computerized operator interface to the chemistry instrument 24 is provided through connections to the programmable workstation 30. Most of the operator interactions with the analyzer take place at workstation 30. It is an external desktop computer located near the chemistry instrument(s) 24. It uses an industry standard operating system and bus structure, plus a hard disk. It is also provided with a custom instrument interface board for each associated chemistry instrument.

Operations required for sample testing of cuvette contents are not carried out in any predetermined sequence dictated by insertion of a sample into the chemistry instrument 24. Instead, workstation 30 serves as random access control means operably connected to the turntable 11, tray 15 and probe arm 17 for selectively transferring liquid from any container on the tray 15 to any cuvette 10 on the turntable 11 according to defined logical priority rules programmed into the workstation.

Operations carried out within the chemistry instrument 24 are timed about a repetitious cycle of operations. Each cycle involves sequentially transferring liquids to an awaiting cuvette 10 on the turntable 11, mixing the liquids, and centrifuging them for test purposes.

A monitor 31 is included within workstation 30 to display data, messages and optional menus for the operator. A keyboard 32 is included for operator input of data and instructions. A printer (not shown) of conventional design can also be provided in the system to record tests results and reports as required.

A plurality of test cuvettes 10 are releasably located within a motor-controlled turntable 11. It is powered by a DC motor 12. Motor 12 can be accurately controlled to (1) selectively index turntable 11 at a chosen angular position about its vertical axis for access to a particular cuvette and/or insertion of new cuvettes or (2) intermittently or reversibly rotate turntable 11 about its axis for mixing the contents of the cuvettes or (3) spin turntable 11 for centrifuging the contents of the cuvettes during photometric analysis.

A liquid transfer module includes a single probe arm 17 movably supported on the instrument 24 about a vertical axis. The outer end of probe arm 17 carries a downwardly extending pipette 18. Pipette 18 is used for transferring liquids between various locations about the chemistry instrument. Its lower or outer end is open for receiving or discharging liquids.

Probe arm 17 is supported and powered by a positioning assembly 19. The positioning assembly 19 has two stepper motors-one for imparting rotational motion to probe arm 17 and one for imparting vertical motion to it. Positioning assembly 19 can selectively move probe arm 17 and pipette 18 both angularly and axially relative to the vertical axis of probe arm 17.

The tip or lower end of pipette 18, while in an elevated condition permitting angular movement about the chemistry instrument 24, projects slightly into an open arcuate groove 29 (FIGS. 2, 3) formed about the cover 34 of the instrument enclosure. Groove 29 is centered about the axis of probe arm 17 and is recessed within cover 34. It overlaps the bottom of pipette 18 to prevent its accidental engagement with the hands of an operator as the pipette travels from one station to the next. The protective overlap of the pipette tip eliminates the danger of accidently impaling adjacent personnel when pipette 18 is subsequently lowered.

A cuvette dispenser module 13 is arranged on the framework of the equipment in a position immediately above the turntable 11. It includes a storage magazine for a plurality of stacks of cuvettes 10. It also includes an apparatus for transferring individual cuvettes 10 from a randomly selectable stack within the magazine 75 to a receiving compartment on turntable 11. Used cuvettes 10 are discarded into a removable cuvette disposal container (not shown) as new cuvettes are delivered to the turntable 11 by operation of a reciprocating ram. The cuvette disposal container can be a bag or bin into which used cuvettes drop when ejected from turntable 11.

The optical system 14 is contained within a housing positioned next to turntable 11. Optical system 14 performs photometric tests on the contents of cuvettes 10 while they are being spun about the turntable axis. The optical system 14 measures both fluorescent emissions and light absorbance by cuvette contents within the turntable 11. Photometric test groups typically supported include routine chemistries, special proteins, therapeutic drugs, and drugs of abuse.

For absorbency tests, the optical system 14 measures radiation at 180 degrees to the incident light. Readings are made at several wavelengths on a diode array, but only those points requested in specified test parameters are processed by the instrument 24. System offsets are subtracted from the results and the sample signal is divided by a reference signal. The negative logarithm of this ratio is the absorbance.

When conducting fluorescent tests, emitted radiation at a wavelength longer than that of the source is measured at 90 degrees to the incident beam. System offsets are subtracted and the intensity is then normalized using a reference signal.

A sample/reagent tray 15 is rotatably mounted about a vertical axis parallel to and spaced from the axis of turntable 11. It is rotatably powered by a stepper motor 16. Tray 15 consists of a circular reagent bottle support surrounded by separate interlocking ring segments 26. The removable ring segments 26 are used to hold reagents and samples required for assay procedures during operation of chemistry instrument 24.

Tray 15 supports a plurality of liquid containers, namely the reagent bottles 25, open cups 35 and open wells 36. The interchangeable ring segments 26 have two alternate configurations. One includes apertures for removably supporting individual sample cups 35. The other includes a plurality of integrally molded sample wells 36.

The individually removable cups 35 serve as containers for test samples supplied to the instrument 24 by the operator within one or more cups within a ring segment 26. Wells 36 are used by the instrument components in conjunction with operation of probe arm 17 for aliquoting of samples from a draw tube and for sample dilution purposes. The probe arm 17 can selectively transfer liquids from one well 36 to a second well 36, from a cup 35 to a well 36, or from a reagent bottle 25 to a well 36.

Figure 3:
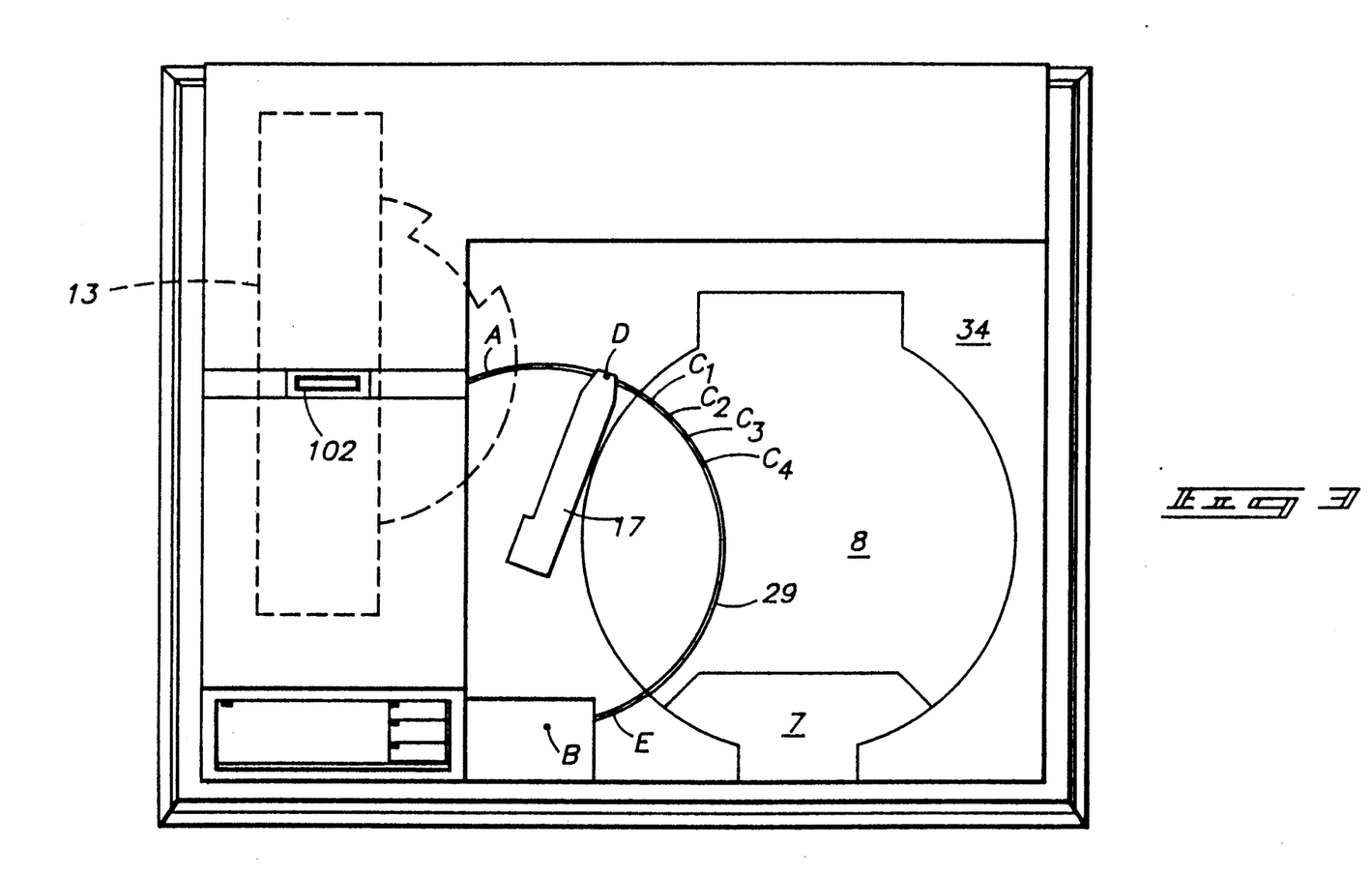
FIG. 3 is a plan view of the chemical instrument enclosure.
Figure 4:
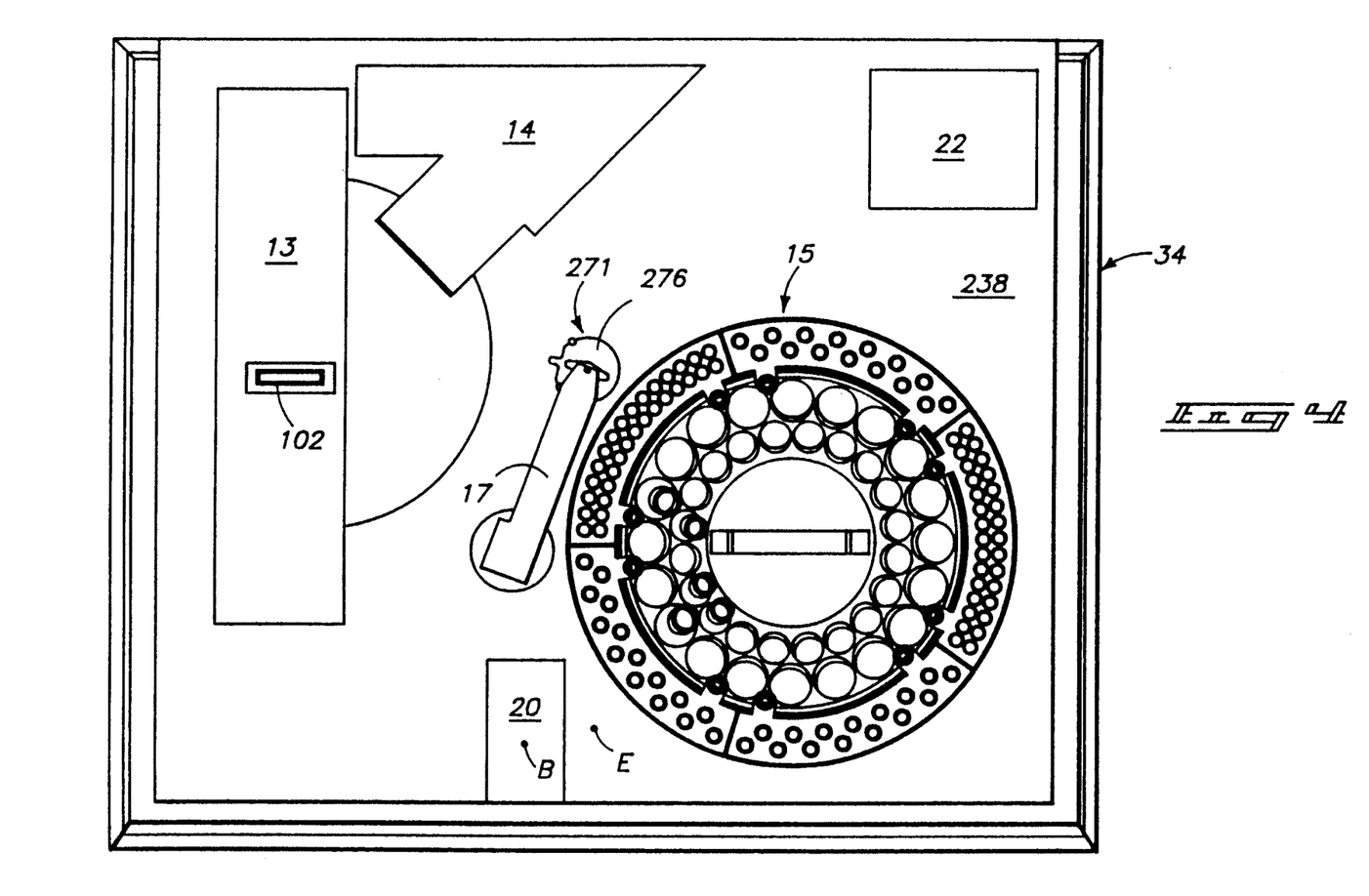
FIG. 4 is a plan view of the chemical instrument enclosure with the cover removed.
Figure 5:
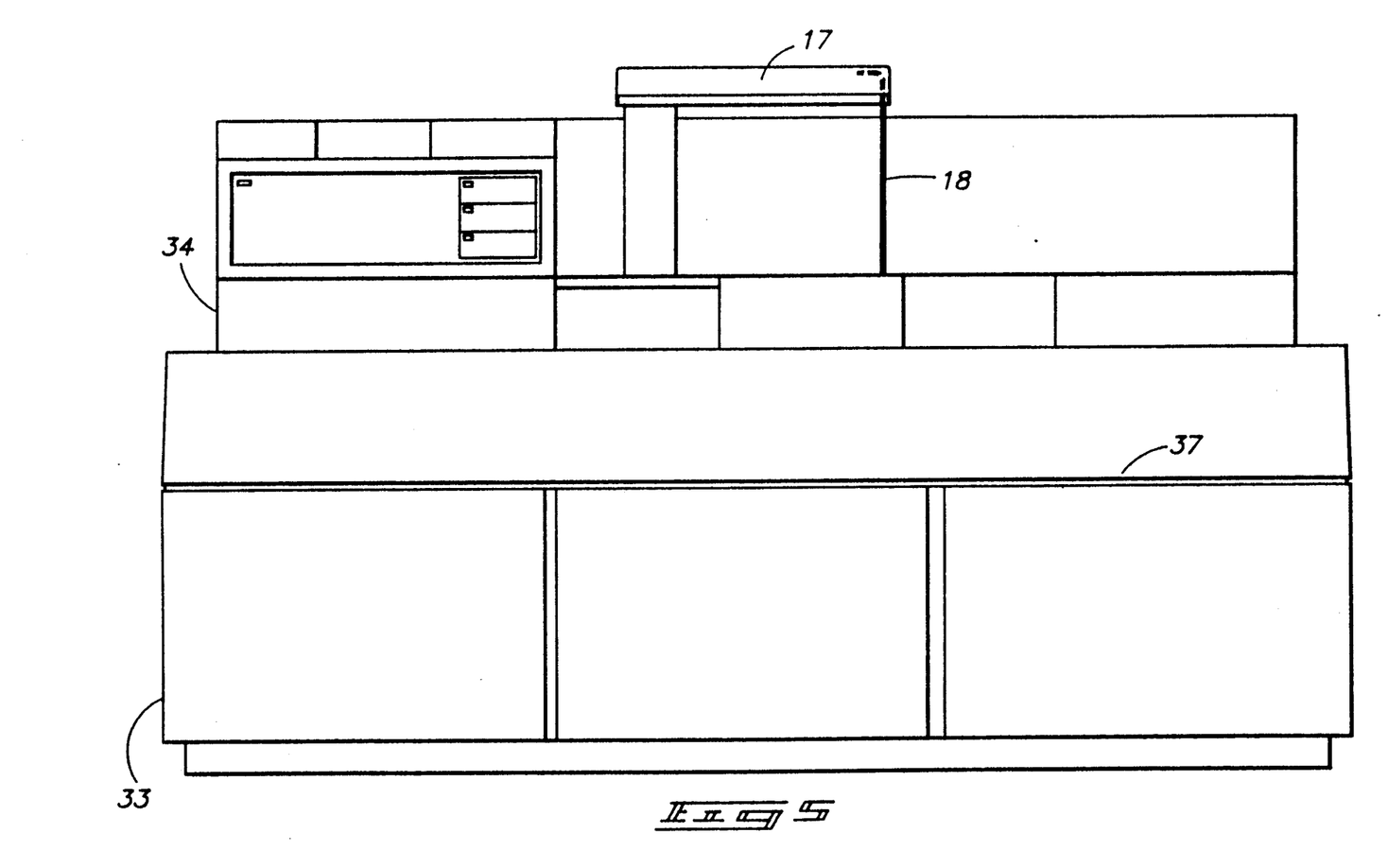
FIG. 5 is a front elevation view of the enclosure.
Figure 6:
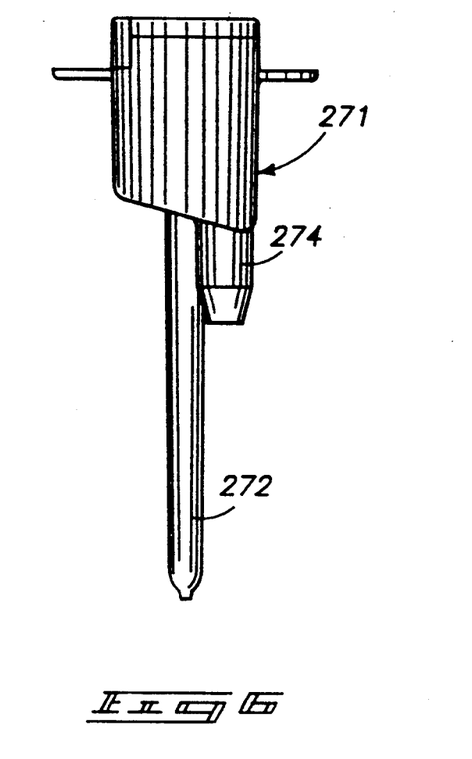
FIG. 6 is a front view of the wash/alignment module.
Figure 7:
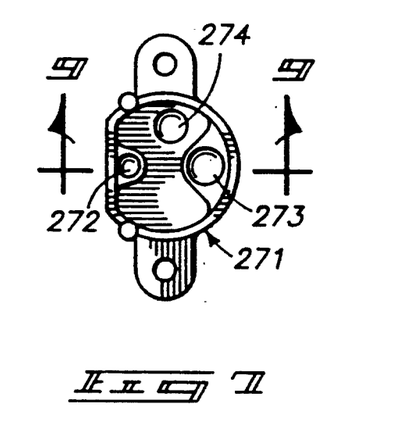
FIG. 7 is a top view with the alignment plate removed.
Figure 8:
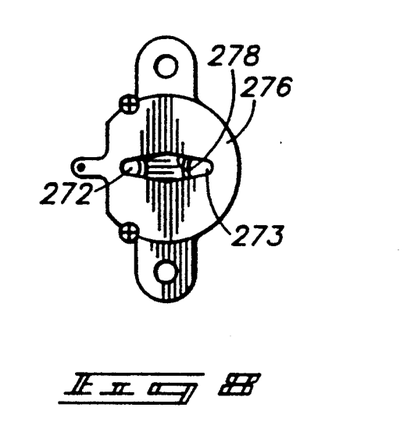
FIG. 8 is a top view with the alignment plate in place.
Figure 9:
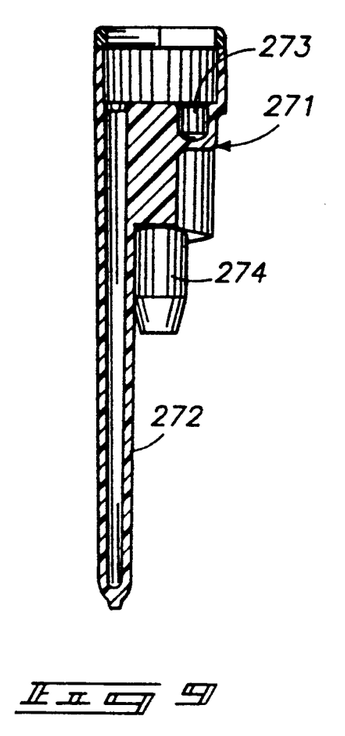
FIG. 9 is a sectional elevation view taken along line 9—9 in FIG. 7.

Access to the sample/reagent tray 15 is provided by a hinged tray access cover 8 formed in the enclosure cover 34. More limited manual access to a single ring segment 26 located at the front of the chemistry instrument 24 is provided by a hinged segment access port 7, which is a sub-assembly of cover 8.

A stepper motor 16 can be operated to index sample/reagent tray 15 to a selected position about its axis with one or more selected containers at one of four container access stations shown in FIG. 3 at locations $C_1$, $C_2$, $C_3$, $C_4$ on the equipment framework. Each container access station intersects the path of pipette 18, which is coincident with groove 29.

Scanning means is provided next to the tray 15 for capturing identifying information from encoded indicia on a container positioned on it.

A cooling system (not shown) for the chemistry instrument 24 incorporates multiple thermoelectric cooling units. These are needed in the areas of the sample/reagent tray 15 and the turntable 11. Heat can be removed from the system by air exchange through a plurality of heat sinks.

A sample tube entry port 20 is provided on the framework for receiving and supporting successive individual draw tubes 27 as they are introduced into the instrument by the operator. Its primary use is to permit the taking of aliquots from positively identified, sealed patient draw tubes. It can also be used for delivery of control liquids from tubes of a similar exterior configuration, whether covered or open. Positive identification can be provided by an encoded label on each draw tube 27. The label is scanned by a bar code reader included within the sample tube entry port 20.

Each draw tube 27, of conventional design, is sealed by a closure at its upper end. Sample tube entry port 20 supports each manually inserted draw tube 27 while pipette 18 pierces the closure 162 to access liquid sample material from the tube interior. Liquid removal from successive tubes 27 occurs at a sample access station B along the arcuate path 29.

Puncturing means are provided within the sample tube entry port 20 for temporarily forming an opening through a closure on a manually-delivered draw tube 27 placed within it. A ram positioned below the puncturing means receives and coaxially orients a manually placed draw tube 27 relative to the puncturing means. It moves the draw tube parallel to a fourth vertical axis (centered along the puncturing means) between a lowered position wherein the draw tube 27 is clear of the puncturing means and a raised position wherein the puncturing means forms a temporary opening through the draw tube closure for subsequent coaxial insertion of the pipette 18. The interior of the draw tube 27 is then accessible by subsequently inserting pipette 18 coaxially through the puncturing means.

A wash/alignment module 21 is located at a fixed position on the framework. Its first purpose is to provide vertical basins within which the lower end surfaces of pipette 18 can be flushed clean during or after liquid transfer cycles. It also supports a conductive sensing plate that verifies both the radial alignment and elevational position of pipette 18 about the pipette axis on the probe arm 17 for monitoring alignment of the pipette. These operations occur at a wash/alignment station D along the arcuate path 29 of pipette 18.

A capacitive sensing circuit is operably connected to the pipette 18 and to conductive members located next to the tray 15 and within the sample tube entry port 20. The sensing circuit detects the level of liquid in a container on the tray or a draw tube 27 as it is approached by the pipette.

A second analytical means, shown as an Ion Specific Electrode (ISE) module 38 of conventional design and operation, is included within the chemistry instrument 24. It is illustrated generally in FIG. 1. Potentiometric tests may be requested and run by the ISE module 38 simultaneously with photometric tests being conducted by the optical system 14.

Samples are delivered to the ISE module 38 by pipette 18 at a sample delivery station E along the arcuate path 29 (FIG. 3). Module 38 can include tests for the presence of a variety of analytes, such as sodium, potassium, chloride, lithium or calcium. For each analyte, all sample types are analyzed in the same manner. The different sample types can be loaded using different dilution factors.

The ISE module 38 consists of electrodes specific to the chosen analyte, a reference electrode and the associated fluid system required to process tested samples. The potentiometric measurement consists of a voltage difference between the analyte's electrode and the reference electrode.

Water is supplied to pipette 18 from a syringe module 22 connected to a water supply container in a container rack 28. The syringe module 22 consists of a volume displacement syringe and associated valves leading to a source of water and a waste water container (not shown). It is used for all aspirations of samples, reagents and diluents in the chemistry instrument 24. The syringe module is of conventional design.

Tubing 23 (FIG. 1) connects syringe module 22 to pipette 18. Tubing 23 contains water that can be moved in opposite directions to receive or discharge liquids at the lower end of pipette 18.

The above components are individually operable under control of a distributed computerized controller system governed by the programmable workstation 30. Workstation 30 is electronically linked to the instrument via a bi-directional communications interface. This interface is used to communicate patient requisitions to the chemistry instrument 24 and to receive the associated test results from the instrument 24. All control functions can be randomly initiated under control of scheduling software and logic to match pending requisition requirements and current instrument status conditions.

The external computer can send patient requisitions to the workstation either individually or in ring segment groups. The workstation can send test results to the external computer.

The control system associated with chemistry instrument 24 includes several dedicated microprocessors and programmable memory devices. They individually operate the system components as prioritized by scheduling software residing in the instrument CPU board. The workstation 30 includes monitoring means for maintaining a current record of the amount of liquid in containers on the sample/reagent tray 15. Controlling software associated with the microprocessors causes the mechanical components of the chemistry instrument 24 to carry out all operations efficiently and effectively without operator intervention, using a random sequence of movements dictated by outstanding test requirements.

The arrangement of operational stations along the arcuate path of pipette 18 permits transfer of liquids from a draw tube 27 at the sample access station B to a well 36 at a container access station $C_1$ or $C_2$ on the sample/reagent tray or from a well 36 to a cuvette 10 at the cuvette access station A on turntable 11. Alternately, pipette 18 can transfer sample diluents (buffers) from the reagent bottles 25 at container access stations $C_3$ or $C_4$ on the sample/reagent tray 15 to a well 36 at a container access station $C_1$ or $C_2$. In addition, it can transfer liquids from one well 36 to another, or from a cup 35 to a well 36 for dilution purposes at container access stations $C_1$ or $C_2$. Direct transfer of reagents from bottles 25 to cuvettes 10 can also take place at cuvette access station A. A wash or pipette alignment procedure can also be periodically accomplished at wash/alignment station D as required. ISE tests are initiated by optional delivery of sample liquids to the ISE station E.

Wash/Alignment Station

The wash/alignment station 21 is detailed in FIGS. 6-10. It comprises a molded basin 271 adapted to be inset into the enclosure platform 238. Basin 271 is covered by a metal plate 276 having an elongated aperture 278 located above an interior deep wash well 272 and tip wash well 273 within the basin 271. Each well 272, 273 is closed at its lower end. The interior of basin 271 has inclined surfaces leading from wells 272, 273 to a common liquid drain 274.

Pipette 18 is washed periodically during operation of the chemistry instrument 24 by inserting its lower end into one of the wells 272 or 273. Water is then flushed through pipette 18 by operation of the syringe module 22. The flushing action of the water cleanses both the interior and exterior surfaces of pipette 18 as it flows downwardly through the pipette and upwardly through the selected well. The waste water is carried away at drain 274 for disposal.

The choice of which well will be used during a specific washing operation will depend upon the depth of liquid contact along the lower end of pipette 18 during the preceding liquid transfer operations. When practical, the analyzer is programmed to utilize the tip wash well 273 as the preferential washing apparatus for a "short wash," since it uses less water and the washing sequence can be carried out more quickly than in the deep wash well 272. A "long wash" is accomplished within the well 272.

The elongated aperture 278 formed in metal plate 276 leads to radiused ends 280 and 281 centered over the respective wells 272 and 273. The inside radius at each end 280 and 281 is slightly greater than the outside radius of pipette 18. Therefore, the aperture 278 does not interfere with normal entrance of pipette 18 into the wash wells 272 and 273.

The metal plate 276 is utilized to periodically check both axial and radial alignment of pipette 18 relative to the supporting probe arm 17. The probe arm 17 is programmed to periodically initiate an alignment test sequence for this purpose. The circuitry for accomplishing this task is described below.

Figure 10:
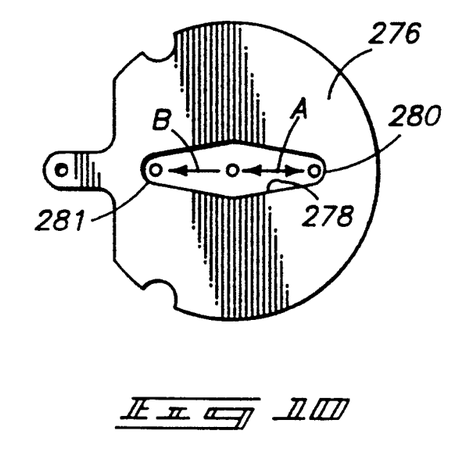
FIG. 10 is an enlarged diagrammatic view illustrating use of the pipette alignment plate.

Each alignment test sequence involves insertion of the pipette tip through the center of aperture 278 and subsequent shifting of pipette 18 to the nominal center position adjacent the radiused end 280 of plate 276 (arrow A in FIG. 10) and then to the nominal center position adjacent to the radiused end 281 (arrow B in FIG. 10).

Any physical engagement between pipette 18 and the plate 276 during the test sequence will be detected electronically and will abort the alignment procedure. This will result in the probe arm 17 positioning the pipette 18 at a realignment location upwardly adjacent to plate 276. A visual mark can be provided above the ISE port E to assist the operator in bending pipette 18 to align it properly.

Assuming that no contact takes place during the back and forth swinging movement of the pipette tip within the aperture 278, and radial alignment of the pipette 18 is therefore confirmed, the probe arm 17 will next proceed to test its axial or elevational alignment with the probe arm 17 and supporting components of the chemistry instrument 24 by detection of the elevation of the lower end of pipette 18. This is accomplished by first moving pipette 18 into physical touching contact against the radiused end 281. When contact has been electrically detected, probe arm 17 can then be raised until the pipette tip just clears the top surface of plate 276. The detection of this elevation is then used as a reference to calibrate the elevation of pipette 18 relative to the platform 238 and all operational equipment supported on it, including the sample tube entry port 20, the sample/reagent tray 15, the ISE module 38, and the cuvette turntable 11.

Utilization of the wash/alignment station 21 can be programmed into any test sequence to either wash the operative end surfaces of pipette 18 and/or to check its radial and/or axial alignment on probe arm 17.

It is to be understood that the functions of washing the pipette surfaces and checking its alignment are independent. They have been combined in the illustrated station only for reasons of economy in space utilization about the supporting platform 238 of enclosure 34. The basin 271 and plate 276 can be separately mounted and used independently from one another when desired.

Capacitive Sensing System

Figure 11:
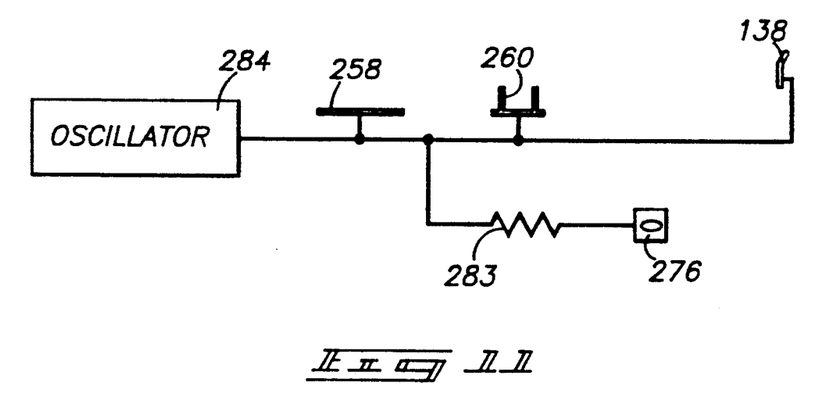
FIG. 11 is a simplified plan view of the sensing components arranged on the supporting platform.
Figure 12:
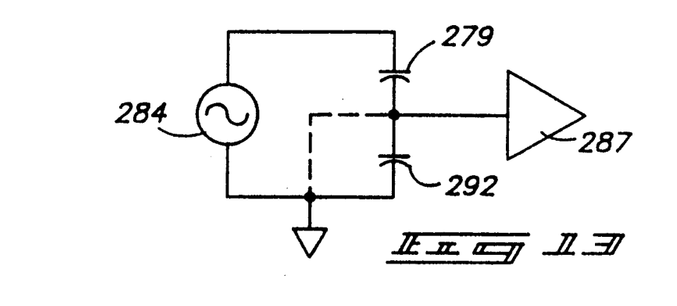
FIG. 12 is a simplified diagram of the wiring connections between the sensing plates and oscillator.

A capacitive sensing system is provided within chemistry instrument 24 for sensing of liquid levels by use of pipette 18, for sensing radial misalignment of pipette 18 and for sensing the elevational position of pipette 18. FIG. 11 is a simplified plan view of the components mounted to platform 238 which are used effectively as plates of a sensing capacitor in the detection circuitry. FIGS. 12-14 diagrammatically illustrate the circuitry involved in this system.

The capacitive sensing system provides a mechanism for dynamically sensing the surface of liquid in a container, such as the reagent bottles 25 mounted within sample/reagent tray 15. The ability to determine the elevation of the surface of the liquid allows the equipment controlling insertion of pipette 18 into liquids to limit surface contact with reagents and samples, thereby minimizing the amount of excess liquid carried at the outside surfaces of pipette 18 and resulting contamination from sample to sample. It also permits the system to maintain an updated inventory of liquid in all containers included in the chemistry instrument 24 and to notify the operator of system requirements in a timely manner.

When liquid is to be drawn from a container, pipette 18 can be lowered relative to the sensed liquid surface elevation, an amount adequate to draw the liquid upwardly into the pipette without risking physical engagement between the pipette tip and the bottom of the container and without unduly submerging the pipette to a depth that is more than necessary for such purposes.

The physical characteristic measured by the system is the capacitance between a liquid within a container and a metal plate in close proximity to the container. The liquid in the container, when contacted by pipette 18, acts as one plate of the measured capacitor, assuming that the liquid has the ability to become ionized or is polar in nature.

Figure 15:
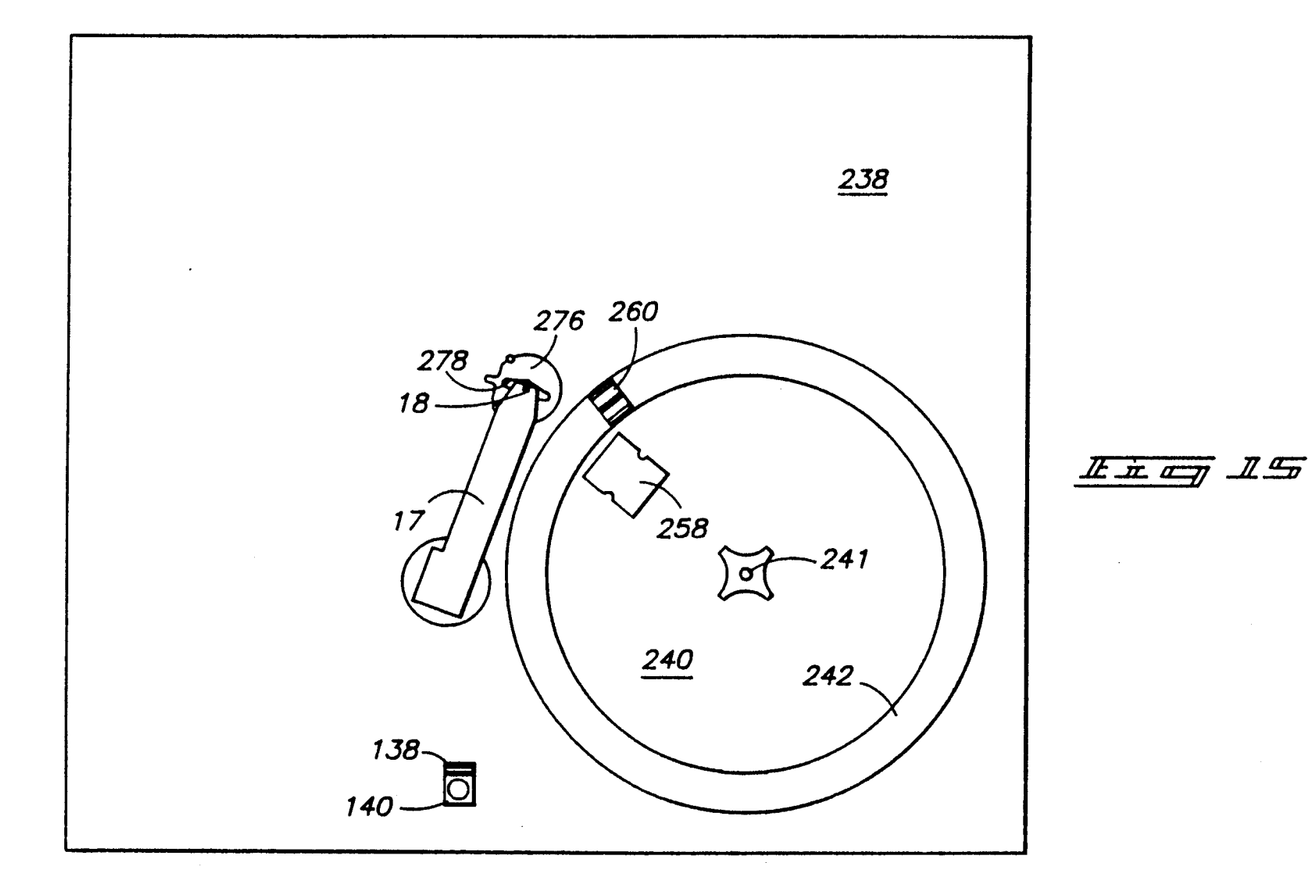
FIG. 15 is a second equivalent circuit diagram.

With respect to fluid level sensing, the system components illustrated in FIG. 15 that measure fluid level are the pipette 18 at the outer end of probe arm 17, the conductive plate 260 located immediately beneath the cups 35 and wells 36 on ring segments 26 mounted to the sample/reagent tray 15, the conductive plate 258 fixed within well 240 immediately beneath the reagent bottles 25 mounted in sample/reagent tray 15, and a conductive plate 138 mounted adjacent to a vertically movable ram 140 that supports a sample tube 27 in the sample tube entry port 20.

In addition, the sensing circuitry is used to detect radial misalignment of pipette 18 when it has been partially inserted through aperture 278 formed in metal plate 276. Interaction between plate 276 and pipette 18 is also used in conjunction with this system to verify the elevational position of the pipette 18 relative to the fixed elements of the chemistry instrument 24 supported on platform 238.

As shown in FIG. 11, the plates 138, 258, 260 and 276 are connected to a driving oscillator 284 in a series circuit. The connections to plates 138, 258 and 260 can be made directly to the drive signal output of oscillator 284. Since pipette 18 will be brought into direct contact with conductive plate 276 during probe alignment procedures, a fixed resistor 283 is provided in series with it to assure that the center frequency of the bandpass filter 288 can be found.

There are three major items included within the capacitive sensor system shown in FIG. 12. They are (a) a gated voltage-controlled oscillator 284, (b) a capacitance measurement jig, situated at one or more locations accessible to the pipette 18, each including a conductive drive plate, and (c) a low input impedance amplifier 287 with a bandpass filter 288 tuned to the output frequency of oscillator 284.

Oscillator 284 provides the drive signal that will ultimately be measured by the detector circuitry connected to pipette 18. It is preferably a sine wave oscillator whose output can be gated.

One significant feature of this circuit is that oscillator 284 is tunable by a microprocessor within the liquid transfer module, which also monitors the frequency of the signals transmitted through pipette 18. This allows for constant fine tuning of the frequency of oscillator 284 so that its output signal is precisely tuned to the center of the band pass filter frequency. The algorithm for tuning oscillator 284 can be run during periods of reduced system activity so as to always maintain optimum system performance and to eliminate adjustments during normal operation of the analyzer.

The ability to control the frequency of the signal produced by oscillator 284 allows fine tuning of the system to optimize the detector circuits. As an example of selectable operational parameters, the oscillator 284 might produce a 262 kHz drive signal and filter 288 might pass only signals at a frequency of 262 kHz.

Each capacitance measurement jig provides the means by which the drive signal from oscillator 284 can be coupled into the liquid-containing portion of the capacitor being measured. When the pipette tip comes into contact with the liquid at the liquid level, denoted by dashed line 286 in FIG. 12, the capacitive coupling between pipette 18 and drive plate 258 will become significantly greater and the transmission of the drive signal from oscillator 284 through the capacitor will increase.

Significant signals received through pipette 18 are coupled into the very low input impedance amplifier 287 connected to a tuned band pass filter that only allows the correct drive signal to be detected. The filter signal is then directed to a detector and output driver circuit 290 connected to the analog/digital input of the controller 310.

The use of a very low input impedance amplifier to receive the signal coupled through the liquid within a reagent bottle 25 tends to eliminate the effects of stray capacitances that might be received in parallel with the capacitance of the container. As an example, a typical capacitance that might be expected by pipette 18 to couple it to a 262 Khz signal source is on the order of 5 to 25 picofarads. However, given the location of the pipette within the chemistry instrument 24, it might encounter stray capacitances 292 from unidentified signal sources 291 that are an order of magnitude greater than that of liquid in a reagent bottle 25. If the amplifier 287 had high input impedance these stray capacitive values would be in parallel with bottle 25 and cause an attenuation of the signal measured at the tip of pipette 18. Further, since the stray capacitances 292 are unpredictable in value, the resulting signal strength would also vary unpredictably because the strays would result in a voltage divider network and the transfer function would be impossible to dependably predict.

To counteract this problem, a very low input impedance amplifier 287 is used to receive the signal from pipette 18 so that the shunt impedances of stray capacitances 292 are very large with respect to amplifier input impedance. In effect this creates a current summing node for the signals so that all input signals are capacitively coupled into a virtual ground. This method allows stray capacitances of many times the capacitances produced within bottle 25 to exist, but they will not affect the load impedance of amplifier 287 since it is already very low. This feature allows extra bottles or an operator to be in close proximity to the container being sensed without confusing operation of the detection circuit. FIGS. 13 and 14 illustrate equivalent circuits when the network described above is measuring a typical reagent bottle capacitance shown at 279 and is connected to a very low input impedance amplifier 287 (FIG. 13) or to a high input impedance amplifier 277 (FIG. 14).

The significant increase in signal strength received from pipette 18 when it comes into contact with liquid within the reagent bottle 25, together with the known elevation of pipette 18 and reagent bottle 25 relative to the common supporting platform 238 of the chemistry instrument 24, permits workstation 30 to compute the remaining volume of liquid within the container, since the interior cross-section of each reagent bottle 25 is known and constant.

In addition to sensing fluid level, the detection circuit shown in FIG. 12 is also used with slotted conductive plate 276 to verify radial alignment of pipette 18 and/or to calibrate the elevation of the pipette tip relative to the supporting platform 238 for the equipment. The physical steps involved in such calibrations are described above with respect to the details of plate 276. The electronic results are quite similar to those used for sensing the level of fluid within reagent bottles 25 (or cups 35 and wells 36). However, because the pipette 18 will physically contact the alignment measuring edge about aperture 278 in the conductive plate 276 if misaligned, and because contact between pipette 18 and plate 276 is used to detect the reference elevation of pipette 18 for calibration purposes, a minimum impedance is assured by resistor 283 in series with plate 276. Therefore, when such contact occurs, there will be a significant decrease in the detected signal level coupled between plate 276 and pipette 18, to allow calibration of the bandpass filter 288 without saturation of the A/D converter within microcomputer 310.

When checking for alignment of pipette 18, it is first lowered through the center of aperture 278 within plate 276. Pipette 18 then swings to one side and is stopped short of contact (if in alignment) with plate 276. The resulting signal received through pipette 18 is then checked to determine whether it remains above the signal that would be passed by the series resistor 283. If there has been no contact, pipette 18 then swings to the opposite side of aperture 278 and the measurement sequence is repeated.

Assuming that no contact with plate 276 is detected, pipette 18 is then moved further to the side and into contact with the end of aperture 278. This results in a strong signal being directed through the pipette 18. Probe arm 17 is next raised upwardly until this signal significantly decreases, indicating a gap between pipette 18 and plate 276. The detection of the end of pipette 18 is used to calibrate the elevation of the pipette tip relative to platform 238 and the system components fixed to it.

Accurate measurement of liquid volume within reagent bottle 25 and accurate radial and axial alignment of pipette 18 relative to the remaining components on the instrument framework allows the pipette 18 to be lowered to a position directly above the inner surfaces within each container used in conjunction with the chemistry instrument 24 as necessary. This enables it to more completely remove liquid from within it.

The control system for the chemistry instrument 24 includes a distributed family of controller microprocessors. They include a Liquid Transfer Module controller (not shown). This microprocessor and its associated circuitry move probe arm 17 vertically and angularly through control of operator 19. Sensors (not shown) associated with probe arm 17 and operator 19 provide signals indicative of the vertical and angular position of probe arm 17 at all times. The transfer module controller also controls operation of the capacitive sensing system shown in FIGS. 11 and 12.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method for monitoring alignment of an electrically conductive pipette supported on a movable probe arm, comprising the following steps:
    positioning the lower end of the pipette above an electrically conductive plate positioned at an alignment station in the path of the pipette, the plate having an alignment measuring edge arranged adjacent an intended path of the pipette;
    moving the pipette relative to the alignment measuring edge during an alignment test; and generating a signal when the pipette contacts the alignment measuring edge.

2. The alignment method of claim 1 wherein the step of moving the pipette involves shifting the probe arm downwardly along the intended path and subsequently pivoting it back and forth about a fixed vertical axis.

3. The alignment method of claim 1 wherein the step of moving the pipette involves shifting the probe arm downwardly along the intended path, subsequently pivoting it about a vertical axis in one angular direction until it contacts the alignment measuring edge, and then raising it upwardly while maintaining such contact.

4. The alignment method of claim 1 wherein the step of moving the pipette involves the following sequence of sub-steps:
   shifting the probe arm downwardly along the intended path; pivoting it back and forth about a fixed vertical axis;
   continuing to pivot it about the vertical axis in one angular direction until it contacts the alignment measuring edge; and
   raising it upwardly while maintaining such contact.

5. A probe alignment apparatus for a chemical analyzer, comprising:
   a fixed framework;
   an alignment station fixed to the framework;
   a vertical pipette having an electrically-conductive exterior and an open lower end;
   probe arm means operably supporting the pipette on the framework for positioning its lower end above the alignment station; and
   an electrically conductive plate positioned at the alignment station in the path of the pipette, the plate having an alignment measuring edge arranged adjacent an intended path of the pipette;
   operator means for moving the pipette relative to the alignment measuring edge during an alignment test; and
   probe detector means for generating a signal when the pipette contacts the alignment measuring edge to indicate that the pipette is not properly positioned relative to the fixed framework.

6. The probe alignment apparatus of claim 5 wherein the probe detector means comprises a capacitive sensing circuit coupled to the pipette and to the plate for detecting changes in capacitance caused by contact between the pipette and the plate during an alignment test.

7. The probe alignment apparatus of claim 5, wherein the probe arm means elevationally mounts the pipette for vertical motion relative to the fixed framework;
   the alignment measuring edge being presented about an aperture formed in the plate.

8. The alignment apparatus of claim 5 wherein the probe arm means movably supports the pipette for motion about a vertical axis on the fixed framework;
   the alignment measuring edge being presented about an elongated aperture formed in the plate and aligned tangentially along the path of the pipette about the vertical axis;
   the probe detector means being operable to monitor the radial position of the pipette relative to the vertical axis.

9. The probe alignment apparatus of claim 5, wherein the probe arm means elevationally mounts the pipette for vertical motion relative to the fixed framework;
   the alignment measuring edge being presented about an aperture formed in the plate;
   the probe detector means being operable to monitor elevational position of the pipette relative to the fixed framework while in engagement with an edge of the aperture.

10. The alignment apparatus of claim 5 wherein the probe detector means comprises:
    oscillator means for applying an oscillating voltage of a selected frequency to the conductive plate; and
    detecting means operatively coupled to the pipette for sensing the oscillating voltage when the pipette is moved into contact with the alignment measuring edge, the detecting means including a low input impedance amplifier amplifying the oscillating voltage conducted by the pipette when the pipette is moved into contact with the alignment measuring edge.

11. The probe alignment apparatus of claim 10 wherein:
    the low input impedance amplifier outputs an amplified oscillating voltage; and
    the detecting means further includes a band pass filter coupled to receive the amplified oscillating voltage from the low input impedance amplifier.

12. The probe alignment apparatus of claim 10 wherein:
    the low input impedance amplifier outputs an amplified oscillating voltage; and
    the detecting means further includes a band pass filter coupled to receive the amplified oscillating voltage from the low input impedance amplifier, the band pass filter passing a defined range of frequencies;
    the probe alignment apparatus further comprising:
    control means operatively coupled to the oscillator means for tuning the oscillator means to generate an oscillating voltage at a selected frequency that is approximately center of the range of frequencies passed by the band pass filter.

13. A pipette wash/alignment apparatus for a chemical analyzer including a wash/alignment station, comprising:
    an upright electrically conductive pipette having a tip leading to an open lower end;
    probe arm means operably supporting the pipette for positioning its lower end above the wash/alignment station and for subsequently moving it relative to the wash/alignment station;
    a pressurized source of wash liquid operably connected to the pipette for selectively discharging the wash liquid from its lower end;
    wash well means located at the wash/alignment station for receiving a lower portion of the pipette;
    probe detection means including a conductive plate arranged across the wash well for monitoring the position of the pipette; and
    oscillator means for applying an oscillating voltage to the conductive plate.

14. The pipette wash/alignment apparatus of claim 13 wherein:
    the wash well has a deep depth sufficient to receive a substantial portion of the pipette during a long wash;
    the pipette wash/alignment apparatus further comprising a second wash well having a shallow depth sufficient to receive only the tip of the pipette during a short wash.

15. The pipette wash/alignment apparatus of claim 13 wherein:

the wash well has a deep depth sufficient to receive a substantial portion of the pipette during a long wash;

the pipette wash/alignment apparatus further comprising a second wash well having a shallow depth sufficient to receive only the tip of the pipette during a short wash;

the probe detection means comprising a conductive plate mounted above the wash wells and having an elongated aperture formed therein, the elongated aperture defining a first radiused end centered over the deep wash well and a second radiused end centered of the shallow wash well.

16. The pipette wash/alignment apparatus of claim 13 wherein the probe detection means comprises a capacitive sensing circuit coupled to the pipette and to the conductive plate for detecting changes in capacitance caused by contact between the pipette and the plate.

17. The pipette wash/alignment apparatus of claim 13 wherein the probe detection means further comprises:
a capacitive sensing circuit coupled to the pipette and to the conductive plate for detecting changes in capacitance caused by contact between the pipette and the plate, the capacitive sensing circuit including a low input impedance amplifier for amplifying the oscillating voltage conducted by the pipette and outputting an amplified oscillating voltage; and
a band pass filter coupled to the low input impedance amplifier for receiving the amplified oscillating voltage.

18. The pipette wash/alignment apparatus of claim 13 wherein the probe detection means further comprises:
a capacitive sensing circuit coupled to the pipette and to the conductive plate for detecting changes in capacitance caused by contact between the pipette and the plate, the capacitive sensing circuit including a low input impedance amplifier for amplifying the oscillating voltage conducted by the pipette and outputting an amplified oscillating voltage;
a band pass filter coupled to the low input impedance amplifier for receiving the amplified oscillating voltage; and
control means operatively coupled to the oscillator means for adjusting the oscillator means to generate an oscillating voltage at a selected frequency.

19. The pipette wash/alignment apparatus of claim 13 wherein the probe detection means further comprises:
a capacitive sensing circuit coupled to the pipette and to the conductive plate for detecting changes in capacitance caused by contact between the pipette and the plate, the capacitive sensing circuit including a low input impedance amplifier for amplifying the oscillating voltage conducted by the pipette and outputting an amplified oscillating voltage;
a band pass filter coupled to the low input impedance amplifier for receiving the amplified oscillating voltage; and
control means operatively coupled to the oscillator means for adjusting the oscillator means to generate an oscillating voltage at a selected frequency that is chosen so as to be at the approximate center of the range of frequencies passed by the band pass filter.

20. The pipette wash/alignment apparatus of claim 19 wherein the selected frequency is approximately 262 Khz.

* * * * *